(12) United States Patent
Hadba et al.

(10) Patent No.: US 7,947,263 B2
(45) Date of Patent: *May 24, 2011

(54) BIOCOMPATIBLE SURGICAL COMPOSITIONS

(75) Inventors: Ahmad R. Hadba, Wallingford, CT (US); Nadya Belcheva, Middletown, CT (US); John Kennedy, Guilford, CT (US); Mark Roby, Killingworth, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 1125 days.

This patent is subject to a terminal disclaimer.

(21) Appl. No.: 11/635,346

(22) Filed: Dec. 6, 2006

(65) Prior Publication Data

US 2007/0128153 A1    Jun. 7, 2007

Related U.S. Application Data

(60) Provisional application No. 60/742,938, filed on Dec. 6, 2005.

(51) Int. Cl.
*A61Q 5/12* (2006.01)
(52) U.S. Cl. ............... 424/78.27; 424/78.37; 424/78.17
(58) Field of Classification Search .................. None
See application file for complete search history.

(56) References Cited

U.S. PATENT DOCUMENTS

| | | |
|---|---|---|
| 3,631,138 A | 12/1971 | Peters |
| 3,773,595 A | 11/1973 | Burba et al. |
| 3,879,493 A | 4/1975 | Mudde |
| 3,903,232 A | 9/1975 | Wood et al. |
| 3,975,550 A | 7/1976 | Fioriti et al. |
| 4,057,535 A | 11/1977 | Lipatova et al. |
| 4,061,662 A | 12/1977 | Marans et al. |
| 4,132,839 A | 1/1979 | Marans et al. |
| 4,169,175 A | 9/1979 | Marans et al. |
| 4,321,350 A | 3/1982 | Lehmann |
| 4,323,491 A | 4/1982 | Veselovsky et al. |
| 4,404,296 A | 9/1983 | Schapel |
| 4,425,472 A | 1/1984 | Howard et al. |
| 4,451,627 A | 5/1984 | Frisch, Jr. et al. |
| 4,477,604 A | 10/1984 | Oechsle, III |
| 4,511,626 A | 4/1985 | Schumacher |
| 4,547,561 A | 10/1985 | Wegner |
| 4,654,409 A | 3/1987 | Shirai et al. |
| 4,681,934 A | 7/1987 | Shibanai et al. |
| 4,722,815 A | 2/1988 | Shibanai |
| 4,740,534 A | 4/1988 | Matsuda et al. |
| 4,743,632 A | 5/1988 | Marinovic |
| 4,762,899 A | 8/1988 | Shikinami |
| 4,804,691 A | 2/1989 | English et al. |
| 4,806,614 A | 2/1989 | Matsuda et al. |
| 4,829,099 A | 5/1989 | Fuller et al. |
| 4,883,837 A | 11/1989 | Zabrocki |
| 4,994,208 A | 2/1991 | McBain et al. |
| 4,994,542 A | 2/1991 | Matsuda et al. |
| 4,997,656 A | 3/1991 | Shikinami et al. |
| 5,065,752 A | 11/1991 | Sessions et al. |
| 5,082,663 A | 1/1992 | Konishi et al. |
| 5,166,300 A | 11/1992 | Rumon et al. |
| 5,169,720 A | 12/1992 | Braatz et al. |
| 5,173,301 A | 12/1992 | Itoh et al. |
| 5,175,228 A | 12/1992 | Wang et al. |
| 5,204,110 A | 4/1993 | Cartmell et al. |
| 5,346,981 A | 9/1994 | Sarpeshkar et al. |
| 5,374,704 A | 12/1994 | Muller et al. |
| 5,389,718 A | 2/1995 | Potter et al. |
| 5,457,141 A | 10/1995 | Matsuda |
| 5,462,536 A | 10/1995 | Braatz et al. |
| 5,574,104 A | 11/1996 | Kolycheck et al. |
| 5,574,123 A | 11/1996 | Bock et al. |
| 5,578,662 A | 11/1996 | Bennett et al. |
| 5,603,798 A | 2/1997 | Bhat |
| 5,672,652 A | 9/1997 | Bhat |
| 5,688,860 A | 11/1997 | Croft |
| 5,703,158 A | 12/1997 | Duan et al. |
| 5,711,958 A * | 1/1998 | Cohn et al. ................ 424/423 |
| 5,717,030 A | 2/1998 | Dunn et al. |
| 5,780,573 A | 7/1998 | Iwata et al. |
| 5,791,352 A | 8/1998 | Reich et al. |
| 5,795,633 A | 8/1998 | Yokoyama et al. |
| 5,869,566 A | 2/1999 | Thomas |
| 5,900,473 A | 5/1999 | Acevedo et al. |
| 5,912,193 A | 6/1999 | Iwata et al. |
| 5,922,809 A | 7/1999 | Bhat et al. |
| 5,948,427 A | 9/1999 | Yamamoto et al. |
| 5,976,305 A | 11/1999 | Bhat et al. |
| 5,990,237 A | 11/1999 | Bentley et al. |
| 6,071,530 A | 6/2000 | Polson |
| 6,103,850 A | 8/2000 | Reichel et al. |
| 6,154,089 A | 11/2000 | Rombach |
| 6,162,241 A | 12/2000 | Coury et al. |

(Continued)

FOREIGN PATENT DOCUMENTS

EP        0 077 192 A2    4/1983

(Continued)

OTHER PUBLICATIONS

European Search Report (EP 06 00 9170).
Margolin A L et al.: "Steroselective Oligomerizations Catalyzed by Lipases In Organic Olvents"; Tetrahedron Letters, vol. 28, No. 15, 1987pp. 1607-1610.
Okumura S. et al.: "Synthesis of Ester Oligomer by AspergillNiger Lipase" Agricultural and Biological Chemistry, vol. 48, No. 11, 1984, pp. 2805-2808.
Lumann N R et al.: The convergent Synthesis of Poly(glycerol-succininc acid) Dendritic Marcomolecules: Chemistry—A European Journal, VCH Publishers, US vol. 9, 2003, pp. 5618-5626.
Database WPI, Section Ch, Week 199442 Derwent Publications Ltd. London, GB; AN 1994-3383493.

(Continued)

*Primary Examiner* — Michael G Hartley
*Assistant Examiner* — James W Rogers

(57) ABSTRACT

Biocompatible synthetic macromer compositions are provided including a first polymer having multiple functional groups and a second functionalized polyurethane prepolymer, which can be employed as an adhesive or sealant for medical/surgical uses.

18 Claims, No Drawings

U.S. PATENT DOCUMENTS

| | | |
|---|---|---|
| 6,197,915 B1 | 3/2001 | Yamana et al. |
| 6,217,894 B1 | 4/2001 | Sawhney et al. |
| 6,235,815 B1 | 5/2001 | Loercks et al. |
| 6,261,544 B1 | 7/2001 | Coury et al. |
| 6,290,729 B1 | 9/2001 | Sleplan et al. |
| 6,296,908 B1 | 10/2001 | Reihs et al. |
| 6,297,349 B1 | 10/2001 | Goldberg et al. |
| 6,312,725 B1 | 11/2001 | Wallace et al. |
| 6,352,710 B2 | 3/2002 | Sawhney et al. |
| 6,395,112 B1 | 5/2002 | Sitzmann et al. |
| 6,395,823 B1 | 5/2002 | Brink et al. |
| 6,461,631 B1 | 10/2002 | Dunn et al. |
| 6,465,001 B1 | 10/2002 | Hubbell et al. |
| 6,465,004 B1 | 10/2002 | Rossi-Montero et al. |
| 6,495,127 B1 | 12/2002 | Wallace et al. |
| 6,512,033 B1 | 1/2003 | Wu |
| 6,555,645 B1 | 4/2003 | Ikeda et al. |
| 6,565,969 B1 | 5/2003 | Lamon et al. |
| 6,576,702 B2 | 6/2003 | Anderle et al. |
| 6,579,952 B1 | 6/2003 | Niki et al. |
| 6,582,713 B2 | 6/2003 | Newell et al. |
| 6,605,666 B1 | 8/2003 | Scholz et al. |
| 6,824,703 B2 | 11/2004 | Lawrey et al. |
| 2002/0028875 A1 | 3/2002 | Anderle et al. |
| 2003/0032734 A1 | 2/2003 | Roby |
| 2003/0035786 A1 | 2/2003 | Hendriks et al. |
| 2003/0044380 A1 | 3/2003 | Zhu et al. |
| 2003/0176615 A1 | 9/2003 | Lawrey et al. |
| 2003/0195293 A1 | 10/2003 | Lubnin et al. |
| 2004/0019178 A1 | 1/2004 | Gross et al. |
| 2004/0023842 A1 | 2/2004 | Pathak et al. |
| 2004/0068078 A1 | 4/2004 | Milbocker |
| 2004/0198901 A1 | 10/2004 | Graham et al. |
| 2004/0198944 A1 | 10/2004 | Meltzer et al. |
| 2004/0242831 A1 | 12/2004 | Tian et al. |
| 2004/0259968 A1 | 12/2004 | Krebs |
| 2005/0004661 A1 | 1/2005 | Lewis et al. |
| 2005/0069573 A1 | 3/2005 | Cohn et al. |
| 2005/0070913 A1 | 3/2005 | Milbocker et al. |
| 2005/0129733 A1 | 6/2005 | Milbocker et al. |
| 2005/0131192 A1 | 6/2005 | Matsuda et al. |
| 2005/0142162 A1 | 6/2005 | Hunter et al. |
| 2005/0147647 A1 | 7/2005 | Glauser et al. |
| 2005/0154148 A1 | 7/2005 | Nakamichi et al. |
| 2005/0266086 A1 | 12/2005 | Sawhney |
| 2007/0128152 A1 | 6/2007 | Hadba et al. |
| 2007/0135605 A1 | 6/2007 | Hadba et al. |
| 2007/0135606 A1 | 6/2007 | Belcheva et al. |

FOREIGN PATENT DOCUMENTS

| | | |
|---|---|---|
| EP | 0 482 467 A2 | 4/1992 |
| EP | 0 488 629 A1 | 6/1992 |
| EP | 0 301 516 B1 | 9/1992 |
| EP | 1 391 205 A1 | 2/2005 |
| EP | 1 719 530 A | 11/2006 |
| EP | 1857489 A1 | 11/2007 |
| GB | 985 144 | 3/1965 |
| GB | 1 143 309 | 2/1969 |
| GB | 1 187 362 | 4/1970 |
| JP | 6263850 | 9/1994 |
| JP | 2002060341 | 2/2002 |
| WO | WO 00/43050 A1 | 7/2000 |
| WO | WO 01/00246 A | 1/2001 |
| WO | WO 01/16210 A | 3/2001 |
| WO | WO 2002/056790 A2 | 7/2002 |
| WO | WO 03/011173 A2 | 2/2003 |
| WO | WO 03/011173 A3 | 5/2004 |
| WO | WO 2004/039323 A2 | 5/2004 |
| WO | WO 2004/039323 A3 | 5/2004 |
| WO | WO 2004/039857 A1 | 5/2004 |
| WO | WO 2004/041890 A1 | 5/2004 |
| WO | WO 2005/032461 A2 | 4/2005 |
| WO | WO 2006/084911 A2 | 8/2006 |
| WO | WO 2006/107957 A2 | 10/2006 |
| WO | WO 2006/128742 A2 | 12/2006 |
| WO | WO 2006/128918 A1 | 12/2006 |
| WO | WO 2007/001448 A2 | 1/2007 |
| WO | WO 2007/067623 A | 6/2007 |

OTHER PUBLICATIONS

Nivasu V M et al.: "In Situ Polymerizable Polyethyleneglycol Containing Polyesterpolyol Acrylates for Tissue Sealant Applications"; Biomaterials 2004 United Kingdom; vol. 25, No. 16, 2004, pp. 3283-3291.

Moon S-Y et al.: Polyurethane/Montorillonite Nancomposites Prepared From Crystalline Polyols, Using 1, 4-Butanediol and Organoclay Hybrids as Chain Extenders: European Polymer Journal, Pergamon Press Ltd. Oxford, GB,; vol. 40, No. 8, Aug. 2004; pp. 1615-16213.

M. J. Song, et al.: "Thermosensitive Sol-Gel Transition Behaviors of Poly(ethylene oide)/ Aliphatic Polyester/Poly(ethylene Oxide) Aqueous Solutions"; Journal of Polymer Science Part A: Polymer Chemistry, vol. 42, No. 3.; Feb. 1, 2004; pp. 772-784.

Mei Xuan Xu et al.: Synthesis and Properties of Unsaturated Polyester Dio-Polyurethanehybrid Polymer Network: Journal of Applied Polymer Science, John Wiley and Sons Inc. New York, US , vol. 54, No. 11, Dec. 12, 1994, pp. 1659-1663.

Oprea S. et al.: "Poly(urethane-methacrylates)s. Synthesis and Characterization"; Polymer, Elsevier Science Publishers B.V., GB, vol. 42, No. 17, Aug. 2001, pp. 7257-7266.

Ferreira, et al., "Modification Of The Biopolymer Castor Oil With Free Isocyanate Groups To Be Applied As Bioadhesive", *International Journal of Biological Macromolecules*, vol. 40, No. 2, pp. 144-152 (2007).

Ferreira, et al., "Development Of A Biodegradable Bioadhesive Containing Urethane Groups", *Journal of Materials Science: Materials in Medicine*, vol. 19, No. 1, pp. 111-120 (2007).

International Search Report from European Application No. EP 08 25 3645 mailed Mar. 5, 2009.

European Search Report for Appln. No. EP 08 25 1790.5 completed Jun. 19, 2009.

European Search Report for Appln. No. EP 08 25 3647 completed Mar. 6, 2009.

International Search Report from Application EP 07 00 1213 dated Sep. 6, 2007.

International Search Report from Application EP 03 77 9244 dated Sep. 26, 2007.

International Search Report from Application PCT/US2006/46553 dated Oct. 31, 2007.

International Search Report from Application PCT/US2006/46554 dated Oct. 31, 2007.

International Search Report (PCT/US2006/46552 dated Nov. 15, 2007).

International Search Report from Application No. PCT/US08/60971 dated Jul. 18, 2008.

European Search Report for EP 06844890.1-2102 date of completion is Jun. 4, 2010 (5 pages).

International Search Report from PCT/US06/47013 dated Oct. 3, 2007.

International Search Report from PCT/US06/46558 dated Nov. 9, 2007.

International Search Report from PCT/US06/47023 dated Nov. 21, 2007.

* cited by examiner

BIOCOMPATIBLE SURGICAL COMPOSITIONS

CROSS-REFERENCE TO RELATED APPLICATIONS

This application claims the benefit of U.S. Provisional Patent Application No. 60/742,938 filed Dec. 6, 2005, the entire disclosure of which is incorporated by reference herein.

TECHNICAL FIELD

The present disclosure relates to biocompatible macromers capable of forming a matrix and the use of these polymers as surgical adhesives or sealants.

BACKGROUND

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that in order for surgical adhesives to be accepted by surgeons, they must possess a number of properties. They must exhibit high initial tack and an ability to bond rapidly to living tissue; the strength of the bond should be sufficiently high to cause tissue failure before bond failure; the adhesive should form a bridge, typically a permeable flexible bridge; and the adhesive bridge and/or its metabolic products should not cause local histotoxic or carcinogenic effects.

Several materials useful as tissue adhesives or tissue sealants are currently available. One type of adhesive that is currently available is a cyanoacrylate adhesive. However, there is the possibility that a cyanoacrylate adhesive can degrade to generate undesirable by-products such as formaldehyde. Another disadvantage with cyanoacrylate adhesives is that they can have a high flexural modulus which can limit their usefulness.

Another type of tissue sealant that is currently available utilizes components derived from bovine and/or human sources. For example, fibrin sealants are available. However, as with any natural material, variability in the material is frequently observed and, because the sealant is derived from natural proteins, there may be viral transmission concerns.

It would be desirable to provide a biological adhesive that is fully synthetic and therefore highly consistent in its properties without the concern of viral transmission. Such a composition should be flexible and biocompatible and should be suitable for use as an adhesive or sealant.

SUMMARY

The present disclosure provides for biocompatible synthetic macromer composition made of at least two polymers. The first polymer possesses one group comprising polysaccharides and/or polyols, a second group comprising a poly(hydroxy) acid, and a functional group which can be an epoxy, halogen, isocyanate, chlorophosphate, anhydride, or a combination thereof. The second polymer that makes up the biocompatible synthetic macromer composition of the present disclosure is a functionalized polyurethane prepolymer having a polymer backbone and degradable or nondegradable bridging groups. In some embodiments the functional groups on the first polymer component are the same, while in other embodiments they are different. Likewise, in some embodiments the functional groups on the second polymer component are the same, while in other embodiments they are different.

In embodiments, a biocompatible synthetic macromer composition of the present disclosure may include a first polymer having the structure

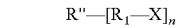

$$R''-[R_1-X]_n$$

wherein R'' can be polysaccharides and/or polyols, $R_1$ is a poly(hydroxy) acid, X is a functional group such as epoxy, halogen, isocyanate, chlorophosphates, anhydrides, and combinations thereof, and n is a number from 1 to 10, and a second polymer including a functionalized polyurethane prepolymer having the structure

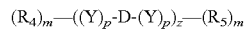

$$(R_4)_m-((Y)_p\text{-}D\text{-}(Y)_p)_z-(R_5)_m$$

wherein Y is a polymer backbone, D is a degradable or non-degradable bridging group, $R_4$ and $R_5$ can be the same or different and can be NCO, CHO, and/or COOH, m is a number from about 1 to about 50, p is a number from about 1 to about 30, and z is a number from about 2 to about 20.

In embodiments, biologically active agents, medicinal agents, and/or enzymes may be added to biocompatible synthetic macromer compositions of the present disclosure.

The biocompatible macromer compositions of the present disclosure may be utilized as adhesives or sealants in a variety of applications, including medical and/or surgical applications. In embodiments, the present disclosure includes methods for closing wounds by applying a biocompatible macromer composition of the present disclosure to a wound and allowing the biocompatible macromer composition to set, thereby closing said wound. Such wounds may include, in embodiments, incisions. Compositions of the present disclosure may also be utilized to fill voids in tissue. In embodiments, compositions of the present disclosure may be utilized to adhere a medical device, such as an implant, to a surface of animal tissue.

DETAILED DESCRIPTION

The present disclosure relates to a synthetic macromer composition for use as a tissue adhesive or sealant, which is biocompatible, non-immunogenic and biodegradable. The biocompatible synthetic macromer composition can be employed to adhere tissue edges, seal air/fluid leaks in tissues, adhere medical devices, i.e. implants, and for tissue augmentation such as sealing or filling voids or defects in tissue. The biocompatible synthetic macromer composition can be applied to living tissue and/or flesh of animals, including humans.

While certain distinctions may be drawn between the usage of the terms "flesh" and "tissue" within the scientific community, the terms are used interchangeably herein as referring to a general substrate upon which those skilled in the art would understand the present adhesive to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic or ascite tissue.

The composition of the present disclosure is a crosslinked biocompatible synthetic macromer composition including a first polymer component, which has at least two or more functional groups, and a second polymer component, which is a functionalized polyurethane prepolymer. The functional groups of the first and second polymer components can bond to one another to form a biocompatible adhesive or sealant. This biocompatible synthetic macromer composition rapidly forms a three dimensional gel-like adhesive matrix, which reduces total surgical/operating time during a medical procedure. The macromer composition can also act as a drug carrier, allowing controlled release and direct delivery of a drug to a specific location in an animal, especially a human. Each polymer component is typically synthetic to reduce or eliminate immuno-reactions in a subject's tissue.

The first polymer component may have at least two, in some embodiments at least three, functional groups. The first polymer can be any biocompatible and/or biodegradable polymer such as, for example, polysaccharides or a polyalkyleneoxide ("PAO") capable of being functionalized. In one embodiment, the first polymer is a polysaccharide including, but not limited to, sorbitol, mannitol, sucrose, dextran, cyclodextrin, etc. In another embodiment, the first polymer is a functionalized PAO such as polyethylene glycol ("PEG"), polyethylene oxide ("PEO"), polypropylene oxide ("PPO"), a polyethylene glycol with lactide linkages, polypropylene glycol ("PPG"), co-polyethylene oxide block or random copolymers, and poloxamers including polyethylene oxide (PEO) copolymers with polypropylene oxide (PPO) such as the triblock PEO-PPO copolymers commercially available as PLURONICS® from BASF Corporation (Mt. Olive, N.J.).

In some embodiments, the first polymer may be a polyethylene oxide, such as a polyethylene glycol ("PEG"). As used herein, polyethylene glycol generally refers to a polymer with a molecular weight of less than 50,000, while polyethylene oxide is used for higher molecular weights. PEGs provide excellent water retention, flexibility and viscosity in the biocompatible synthetic macromer composition of the present disclosure. Most often, the PEG is modified to produce a multi-functional material.

The first polymer can have a branched or star configuration for improved biodegradability. The molecular weight of the first polymer can be from about 500 to about 20,000, in embodiments from about 1,000 to about 10,000, and typically from about 2000 to about 5000.

Polymers can be functionalized to have multiple pendant groups according to any method known to those skilled in the art, including, for example, in Chapter 22 of Poly(ethylene Glycol) Chemistry: Biotechnical and Biomedical Applications, J. Milton Harris, ed., Plenum Press, NY (1992). Various forms of PAOs, in particular PEGs, are commercially available from providers which include, for example, Shearwater Polymers, Inc., Huntsville, Ala., and Texaco Chemical Company, Houston, Tex. Suitable functional groups which can be added to the PAO include epoxy, halogen, isocyanate, chlorophosphates, and anhydrides.

In one embodiment, the first polymer can be synthesized utilizing a multiple step approach. In one embodiment, the polymer can be reacted with a diisocyanate to provide a first polymer having an isocyanate group, i.e.,

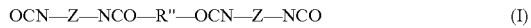

OCN—Z—NCO—R"—OCN—Z—NCO    (I)

wherein R" is a polysaccharide as described above or a polyol, such as a polyalkylene oxide as described above and Z is the core of the diisocyanate which can include, in embodiments, aromatic groups, aliphatic groups, and/or alicyclic groups. In some embodiments R" is a polyethylene glycol, such as a methoxy polyethylene glycol ("mPEG").

Suitable diisocyanates which may be utilized to produce this cyano-terminated polyalkylene oxide include, but are not limited to, aromatic diisocyanates such as 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenylisocyanate) or tetramethylxylylene diisocyanate; aliphatic diisocyanates such as tetramethylene diisocyanate, hexamethylene diisocyanate, lysine diisocyanate, 2-methylpentane-1,5-diisocyanate, 3-methylpentane-1,5-diisocyanate or 2,2,4-trimethylhexamethylene diisocyanate; and alicyclic diisocyanates such as isophorone diisocyanate, cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate or commercially available DESMODURS® from Bayer Material Science. An aliphatic diisocyanate, such as hexamethylene diisocyanate, can be useful in some embodiments.

The resulting isocyanate-terminated polymer may, in turn, be reacted with a polyhydric alcohol such as D-sorbitol, D-mannitol, tris(hydroxymethyl)aminomethane (also known as 2-amino-2-(hydroxymethyl)-1,3-propanediol), enterodiol, cyclodextrins, etc. to form a first polymer having multiple hydroxy groups, i.e.,

R"—(OH)$_n$    (II)

where R" is a member of the group selected from polysaccharides and polyols and n is a number from about 1 to about 10. Suitable polysaccharides include, but are not limited to, sorbitol, mannitol, sucrose, dextran, cyclodextrin, etc. Suitable polyols include, but are not limited to, polyalkylene oxides, polyvinyl alcohols, etc.

The polymer having multiple hydroxy groups may then, in turn, be reacted with hydroxy acids such as lactic acid, glycolic acid, etc., or used in a ring opening polymerization of glycolide, lactide, p-dioxanone, or ε-caprolactone, to form a polyalkylene oxide having multiple poly(hydroxy) acid/hydroxy groups. The poly(hydroxy) acid (PHA) can be polyglycolic acid (PGA), polylactic acid (PLA), polycaprolactone (PCL), poly-p-dioxanone (PPD) and copolymers thereof. Thus, the resulting formula can be

R"—(R$_1$—OH)$_n$    (III)

where R" is as defined above, R$_1$ is a poly(hydroxy) acid, and n is a number from about 1 to about 10.

This polymer having multiple poly(hydroxy) acid/hydroxy groups may, in turn, be reacted with suitable compounds including epichlorohydrin, diisocyanates, dichlorophosphates to form the functionalized first components of the macromer composition of the present disclosure. In embodiments the first components of the compositions of the present disclosure possess multiple functional groups, which can be the same or different.

In one embodiment, where the first polymer possessing multiple poly(hydroxy) acid/hydroxy groups is reacted with epichlorohydrin, functionalized first components produced include, for example,

R"—[R$_1$-epoxy]$_n$,    (IV)

R"—[R$_1$—NCO]$_n$,    (V)

R"—[R$_1$—Cl]$_n$    (VI)

and combinations and mixtures thereof, wherein R", R$_1$ and n are as defined above.

In another embodiment, the first polymer possessing multiple poly(hydroxy) acid/hydroxy groups can be reacted with any diisocyanate identified above thereby producing a compound of formula (VII) above.

Thus, in one embodiment the first polymer component of the present disclosure has the general formula $$R''-[R_1-X]_n \quad (VII)$$

where R'', $R_1$, and n are as defined above, and X is a functional group including, but not limited to, epoxy, halogen, isocyanate, chlorophosphates, anhydrides, and combinations thereof.

As noted above, the first polymer may have a branched or star configuration. Thus, the first polymer may have multiple functional groups which, in one embodiment, may be the same, while in another embodiment the multiple functional groups on the first polymer component may be different.

The first polymer component may be present in the biocompatible synthetic macromer composition of the present disclosure in amounts from about 1% to about 50% by weight of the biocompatible synthetic macromer composition, in embodiments from about 2% to about 30% by weight of the biocompatible synthetic macromer composition, typically from about 5% to about 20% by weight of the biocompatible synthetic macromer composition.

The second polymer component of the biocompatible synthetic macromer composition of the present disclosure is a functionalized polyurethane prepolymer, which adds elasticity and/or strength to the final biocompatible synthetic macromer composition. The reactive functional groups present on the second polymer component can be biocompatible groups such as NCO, CHO, COOH, epoxy, and the like. In one embodiment, the reactive group on the second polymer component is NCO.

In one embodiment, the functionalized polyurethane prepolymer can be formed by reacting a diisocyanate and a polyol to form a polyurethane of the general formula:

$$OCN-(R_2-NH-CO-O-R_3-OCONH)_m-R_2-NCO \quad (VIII)$$

wherein $R_2$ can be an aromatic group an aliphatic group, or an alicyclic group, $R_3$ can be a diol-PEG or PCL-diol, and m can be a number from about 1 to about 50, in embodiments from about 10 to about 30.

Suitable diisocyanates for use in producing the second polymer component in accordance with the present disclosure include those used in producing the first polymer component. Such diisocyanates include, but are not limited to, aromatic diisocyanates such as 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenylisocyanate) or tetramethylxylylene diisocyanate; aliphatic diisocyanates such as tetramethylene diisocyanate, hexamethylene diisocyanate, lysine diisocyanate, 2-methylpentane-1,5-diisocyanate, 3-methylpentane-1,5-diisocyanate or 2,2,4-trimethylhexamethylene diisocyanate; and alicyclic diisocyanates such as isophorone diisocyanate, cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate or commercially available DESMODURS® from Bayer Material Science.

Suitable polyols which can be used to produce the functionalized polyurethane prepolymer include organic compounds containing at least two free hydroxyl groups which are capable of reacting with isocyanate groups. Examples of such organic compounds include polyester, polyester amide, polycarbonate, polyacetal and polyether polyols. Suitable compounds may include, for example, those containing two hydroxyl groups, such as polyester diols or polycarbonate diols.

Examples of polyester polyols which can be used to prepare the polyurethane prepolymer include linear polyester diols or weakly branched polyester polyols prepared from aliphatic, cycloaliphatic or aromatic dicarboxylic or polycarboxylic acids or anhydrides thereof, such as succinic, glutaric, adipic, pimelic, suberic, azelaic, sebacic, nonane dicarboxylic, decane dicarboxylic, terephthalic, isophthalic, o-phthalic, tetrahydrophthalic, hexahydrophthalic or trimellitic acid, and acid anhydrides, such as o-phthalic, trimellitic or succinic anhydride or a mixture thereof; which are then combined with polyhydric alcohols such as, e.g., ethanediol, diethylene, triethylene, tetraethylene glycol, 1,2-propanediol, dipropylene, tripropylene, tetrapropylene glycol, 1,3-propanediol, butane-1,4-diol, butane-1,3-diol, butane-2,3-diol, pentane-1,5-diol, hexane-1,6-diol, 2,2-dimethyl-1,3-propanediol, 1,4-dihydroxycyclohexane, 1,4-dimethylol cyclohexane, octane-1,8-diol, decane-1,10-diol, dodecane-1,12-diol, or mixtures thereof, optionally with the additional use of higher-functional polyols, such as trimethylol propane or glycerol.

Examples of polyhydric alcohols for production of the polyester polyols also include cycloaliphatic and/or aromatic dihydroxyl and polyhydroxyl compounds. Instead of free polycarboxylic acid, the corresponding polycarboxylic anhydrides or corresponding polycarboxylic acid esters of alcohols or mixtures thereof can also be used to produce the polyesters.

Polyester polyols suitable for use herein to prepare the polyurethane prepolymer can also be homopolymers or copolymers of lactones, which may be obtained by reacting lactones or lactone mixtures, such as butyrolactone, ε-caprolactone and/or methyl ε-caprolactone, with suitable difunctional and/or higher functional initiator molecules, such as the polyhydric alcohols mentioned above.

Polycarbonates having hydroxyl groups are also suitable as polyhydroxyl components to prepare the polyurethane prepolymer, and include those that can be produced by reacting diols such as 1,4-butanediol and/or 1,6-hexanediol with diaryl carbonates, e.g., diphenyl carbonate and dialkyl carbonates such as dimethyl carbonate or phosgene.

Examples of polyether polyols that may be used to prepare the polyurethane prepolymer include the polyaddition products of styrene oxides, alkylene oxides such as ethylene oxide, propylene oxide, and butylene oxide, tetrahydrofuran, epichlorohydrin, and their co-addition and graft products, as well as the polyether polyols obtained by condensation of polyhydric alcohols or mixtures thereof and by alkoxylation of polyhydric alcohols, amines and aminoalcohols.

In some embodiments, the polyols utilized to prepare the polyurethane prepolymer can include diols such as polyethylene glycol, 1,2- or 1,3-propanediol, 1,2-, 1,3- or 1,4-butanediol, 1,2-, 1,3-, 1,4- or 1,5-pentanediol, 1,2-, 1,3-, 1,4-, 1,5- or 1,6-hexanediol, neopentyl hydroxypivalate, neopentyl glycol, diethylene glycol, 1,2-, 1,3- or 1,4-cyclohexanediol, 1,2-, 1,3- or 1,4-cyclohexanedimethanol, trimethylpentanediol, ethylbutylpropanediol or the positionally isomeric diethyloctanediols.

The second polymer, i.e., the polyurethane prepolymer, may include bridging groups which can be degradable or nondegradable and contribute to the adhesive and/or crosslinking properties of the final biocompatible synthetic macromer composition. Suitable bridging groups which can be added to the second polymer include, for example, cyclodextrin, sorbitol, polyphenols and polyglycerols. In one embodiment, cyclodextrin is included as a bridging group in the second polymer component of the present disclosure.

Thus, in one embodiment the second polymer component, i.e., the functionalized polyurethane prepolymer, is of the general formula:

$$(R_4)_m-((Y)_p-D-(Y)_p)_z-(R_5)_m \qquad (IX)$$

where Y is a PAO backbone, in embodiments a polyethylene glycol, D is the bridging group as described above, m is a number from about 1 to about 50, in embodiments from about 10 to about 30, p is a number from about 1 to about 30, z is a number from about 2 to about 20, and $R_4$ and $R_5$ can be the same or different and are reactive groups such as NCO, CHO, COOH, epoxy, and the like. Other useful components can also be combined to the second polymer or the final polymer, as discussed below.

The second polymer component may be present in the biocompatible synthetic macromer composition of the present disclosure in amounts from about 5% to about 80% by weight of the macromer composition, in embodiments from about 10% to about 60% by weight of the macromer composition, typically from about 20% to about 40% by weight of the macromer composition.

Once obtained, the first and second polymers can then be combined to form the biocompatible, bioabsorbable synthetic macromer composition. In one embodiment, the first and second polymers are combined in situ in the presence of an amine cross-linker to form the biocompatible synthetic macromer composition of the present disclosure. Suitable amines which may be utilized as the amine cross-linker include diamines, polyether diamines, aromatic amines, polyamines, and polyamidoamines.

Specific examples of suitable amines which may be utilized in the synthesis of the macromer composition of the present disclosure include, but are not limited to, ethylene diamine, hexamethylene diamine, isomers of hexamethylene diamine, diethylene triamine, triethylene tetramine, tetraethylene pentamine, bishexamethylene triamine, N,N'-Bis(3-aminopropyl)-1,2-ethane diamine, N-(3-Aminopropyl)-1,3-propane diamine, N-(2-aminoethyl)-1,3 propane diamine, cyclohexane diamine, isomers of cyclohexane diamine, 4,4'-methylene biscyclohexane amine, 4'4'-methylene bis(2-methylcyclohexanamine), isophorone diamine, and phenalkylene polyamines. In some embodiments tertiary amines such as dimethylaminopropylamine and pyridine may be used as the amine cross-linker.

Examples of useful aromatic amines which may be used as the amine cross-linker in the synthesis of the macromer composition of the present disclosure include di-(4-aminophenyl) sulfone, di-(4-aminophenyl)ether, 2,2-bis(4-aminophenyl propane, 4,4'-diamino diphenylmethane, 3,3'-dimethyl-4,4'-diaminodiphenyl methane, m-phenylene diamine, p-phenylene diamine, m-xylylene diamine, toluene diamine, 4,4'-methylene dianiline, benzidine, 4,4'-thiodianiline, 4-methoxy-1,3-phenyldiamine, 2,6-diaminopyridine, and dianisidine.

Examples of polyether diamines which may be utilized as the amine cross-linker in the synthesis of the macromer composition of the present disclosure include 4,9-dioxadodecane-1,12-diamine, 4,7,10-trioxatridecane-1,12-diamine, bis(3-amino propyl)polytetrahydrofurans of varying molecular weights, and commercially available amines from Texaco Chemical Co. under the JEFFAMINE® brand as D230, D400, D2000, and T403. Other amines which may be used include spermine (N-(3-aminopropyl)-1,4-butanediamine), spermidine (N,N'-bis(3-aminopropyl)-1,4-butanediamine), Bis(3-propylamino)amine, and PEG-SP-polymer conjugates.

In other embodiments, a polyalkylene oxide such as polyethylene glycol with two amine functional groups may be utilized as the amine cross-linker in the synthesis of the macromer composition of the present disclosure.

To prepare the biocompatible synthetic macromer composition, the first polymer may be combined with the second polymer to form a three-dimensional crosslinked matrix as a result of the reaction between the functional groups on the first polymer with the functional groups on the second polymer. The addition of an amine cross-linker can enhance the formation of the biocompatible synthetic macromer composition of the present disclosure.

Where utilized, an amine cross-linker may be applied in an amount sufficient to enhance the polymerization of the two polymer components which, in some embodiments, can be in an amount from about 0.1 to about 20 percent by weight of the biocompatible synthetic macromer composition, typically from about 1 to about 10 percent by weight of the biocompatible synthetic macromer composition.

This resulting biocompatible synthetic macromer composition can be used in a medical/surgical capacity in place of, or in combination with, sutures, staples, clamps and the like. In one embodiment, the biocompatible synthetic macromer composition can be used to seal or adhere delicate tissue together, such as lung tissue, in place of conventional tools that may cause mechanical stress. The resulting biocompatible synthetic macromer composition can also be used to seal air and/or fluid leaks in tissue as well as to prevent post-surgical adhesions and to fill voids and/or defects in tissue.

The concentrations of the first polymer and the second polymer can vary depending upon a number of factors, including the types and molecular weights of the particular polymers used and the desired end use application, i.e., an adhesive or sealant.

The use of higher concentrations of both the first and second polymers may result in the formation of a more tightly crosslinked biocompatible synthetic macromer composition, producing a stiffer and stronger gel matrix. As such, biocompatible synthetic macromer compositions of the present disclosure intended for use in tissue augmentation generally use higher concentrations of both the first and second polymers. Biocompatible synthetic macromer compositions of the present disclosure intended for use as bioadhesives or for the prevention of post-surgical adhesions need not be as firm and may therefore contain lower polymer concentrations.

Biologically active agents may be included in the biocompatible synthetic macromer compositions of the present disclosure. For example, naturally occurring polymers, including proteins such as collagen and derivatives of various naturally occurring polysaccharides such as glycosaminoglycans, can be incorporated into the macromer composition of the present disclosure. When these other biologically active agents also contain functional groups, the groups react with the functional groups on the first and/or second polymer components of the macromer composition of the present disclosure. For example, when the naturally occurring polymer possesses nucleophilic groups such as primary amino groups, the electrophilic groups on the second polymer component of the composition of the present disclosure can react with these primary amino groups as well as the nucleophilic groups on the first polymer component, thereby incorporating the additional components into the final polymer matrix. Similarly, electrophilic groups on the second polymer component of the present disclosure can react with primary amino groups on lysine residues found on collagen and its derivatives, or thiol groups on cysteine residues of certain naturally occurring proteins, thereby incorporating the additional biologically active agents into the final polymer matrix.

A variety of optional ingredients including medicinal agents may also be added to the biocompatible synthetic macromer composition of the present disclosure. For example, a phospholipid surfactant that provides antibacterial stabilizing properties and helps dispense other materials in the biocompatible synthetic macromer composition may be added to the macromer composition of the present disclosure. Other medicinal agents which may be added include antimicrobial agents, colorants, preservatives, or medicinal agents (such as, for example, protein and peptide preparations, antipyretic, antiphlogistic and analgesic agents, anti-inflammatory agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilator agents, antiviral agents and dysuric agents).

Imaging agents such as iodine or barium sulfate, or fluorine, can also be combined with the biocompatible synthetic macromer composition of the present disclosure to allow visualization of the surgical area through the use of imaging equipment, including X-ray, MRI, and CAT scan.

Additionally, an enzyme may be added to the biocompatible synthetic macromer composition of the present disclosure to increase its rate of degradation. Suitable enzymes include, for example, peptide hydrolases such as elastase, cathepsin G, cathepsin E, cathepsin B, cathepsin H, cathepsin L, trypsin, pepsin, chymotrypsin, γ-glutamyltransferase (γ-GTP) and the like; sugar chain hydrolases such as phosphorylase, neuraminidase, dextranase, amylase, lysozyme, oligosaccharase and the like; oligonucleotide hydrolases such as alkaline phosphatase, endoribonuclease, endodeoxyribonuclease and the like. In some embodiments, where an enzyme is added, the enzyme may be included in a liposome or microsphere to control the rate of its release, thereby controlling the rate of degradation of the biocompatible synthetic macromer composition of the present disclosure. Methods for incorporating enzymes into liposomes and/or microspheres are known to those skilled in the art.

The biocompatible synthetic macromer compositions of the present disclosure can be used in human and animal medical applications including, but not limited to, wound closure (including surgical incisions and other wounds), adhesives for medical devices (including implants), sealants and void fillers, and embolic agents.

The biocompatible synthetic macromer composition can be dispensed from a conventional adhesive dispenser, which typically provides mixing of the first and second polymers prior to the dispenser. Such dispensers are disclosed, for example, in U.S. Pat. Nos. 4,978,336, 4,361,055, 4,979,942, 4,359,049, 4,874,368, 5,368,563, and 6,527,749, the disclosures of which are incorporated herein by reference.

In other embodiments, especially where the biocompatible synthetic macromer composition of the present disclosure is to be utilized as a void filler or sealant to fill a defect in an animal's body, it may be advantageous to more precisely control the conditions and extent of cross-linking; in such a case, it may be desirable to partially cross-link the composition prior to its use to fill a void in animal tissue. In such a case the composition of the present disclosure may be applied to the void or defect and allowed to set, thereby filling the void or defect.

The biocompatible synthetic macromer composition of the present disclosure can be used for a number of different applications. These applications include using the adhesive to bind tissue together either as a replacement of, or as a supplement to, sutures, staples, tapes and/or bandages. Use of the biocompatible synthetic macromer composition can eliminate or substantially reduce the number of sutures normally required during current practices, and eliminate the subsequent need for removal of staples and certain types of sutures and thus can be useful for use with delicate tissues where sutures, clamps or other conventional tissue closure mechanisms may cause further tissue damage.

Additional applications of the biocompatible synthetic macromer composition include sealing tissues to prevent or control blood, or other fluid leaks, at suture or staple lines. In another embodiment, the biocompatible synthetic macromer composition can be used to attach skin grafts and position tissue flaps during reconstructive surgery. In still another embodiment, the biocompatible synthetic macromer composition can be used to close tissue flaps in periodontal surgery.

To effectuate the joining of two tissue edges, the two edges are approximated, and the first polymer is combined with the second polymer and applied thereto, optionally with an amine cross-linker. Without wishing to be bound by any theory, it is believed that upon mixing with an amine cross-linker, the two polymers crosslink with each other thereby forming a hydrogel. The crosslinking reaction is rapid, generally taking less than one minute. In this case the macromer the composition of the present disclosure can be used as an adhesive to close a wound, including a surgical incision. In such a case, the macromer composition of the present disclosure can be applied to the wound and allowed to set, thereby closing the wound.

In another embodiment, the biocompatible synthetic macromer composition of the present disclosure may be used to adhere a medical device to tissue, rather than secure two edges of tissue. In some cases the medical device may include a coating of the first polymer of the macromer composition, or the second polymer of the macromer composition. In some aspects, the medical device includes an implant. Other medical devices include, but are not limited to, pacemakers, stents, shunts and the like. Generally, for adhering a device to the surface of animal tissue, the composition of the present disclosure can be applied to the device, the tissue surface or both. The device, biocompatible synthetic macromer composition, and tissue surface are then brought into contact with each other and the macromer composition is allowed to set, thereby adhering the device and surface to each other.

The present biocompatible synthetic macromer composition can also be used to prevent post surgical adhesions. In such an application, the biocompatible synthetic macromer composition is applied and cured as a layer on surfaces of internal tissues in order to prevent the formation of adhesions at a surgical site during the healing process. In addition to the formation of adhesion barriers, the composition of the present disclosure may be utilized to form implants such as gaskets, buttresses, or pledgets for implantation.

When used as a sealant, the biocompatible synthetic macromer composition of the present disclosure can be used in surgery to prevent or inhibit bleeding or fluid leakage both during and after a surgical procedure. It can also be applied to prevent air leaks associated with pulmonary surgery. The biocompatible synthetic macromer composition can be applied directly to the desired area in at least an amount necessary to seal off any defect in the tissue and seal off any fluid or air movement.

Application of the biocompatible synthetic macromer composition with or without other additives, can be done by any conventional means. These include dripping, brushing, or other direct manipulation of the adhesive on the tissue surface, or spraying of the biocompatible synthetic macromer composition to the surface. In open surgery, application by hand, forceps or the like is contemplated. In endoscopic surgery, the biocompatible synthetic macromer composition can be delivered through the cannula of a trocar, and spread at the site by any device known in the art.

The present biocompatible synthetic macromer composition has a number of advantageous properties. The resulting biocompatible synthetic macromer compositions of the present disclosure are safe and biocompatible, possess enhanced adherence to tissue, are biodegradable, have enhanced hemostatic potential, have low cost, and are easy to prepare and use. By varying the selection of the polymer components, the strength and elasticity of the biocompatible synthetic macromer composition can be controlled, as can the gelation time.

The biocompatible synthetic macromer composition rapidly forms a compliant gel matrix, which ensures stationary positioning of tissue edges or implanted medical devices in the desired location and lowers overall required surgical/application time. The biocompatible synthetic macromer composition exhibits little or no swelling upon gel matrix formation, and therefore retains the positional integrity of the aligned tissue edges and/or location of a medical device. The biocompatible synthetic macromer composition forms strong cohesive bonds, based in part on a low percent of water content as compared to other adhesives. It exhibits excellent mechanical performance and strength, while retaining the necessary pliability to adhere living tissue. This strength and pliability allows a degree of movement of tissue without shifting the surgical tissue edge. Additionally, the biocompatible synthetic macromer composition is biodegradable, allowing the degradation components to pass safely through the subject's body.

In order that those skilled in the art may be better able to practice the features of the present disclosure described herein, the following examples are provided to illustrate, but not limit, the features of the present disclosure.

EXAMPLE 1

Activation of methoxy-PEGs by condensation with hexamethylene diisocyanate (HMDI). A solution of mPEG and triethylamine (catalyst) was prepared in 300 g chloroform. HMDI was then added to this solution. The reaction mixture (10% w/v) was heated under reflux (temperature of 60-65° C.) for 5-6 hours. The resulting polymer was isolated by precipitation in petroleum ether/diethyl ether ("PE/ether") at a 1:1 ratio. The precipitate was washed with PE/ether and re-precipitated 2 times with ether. The final product was dried under vacuum. The yield obtained was >90%; NMR, FTIR, and DSC analysis confirmed the production of the polymer. Table 1 below details the compounds utilized to produce this polymer, i.e., mPEG-OCONH$(CH_2)_6$—NCO.

TABLE 1

| | Starting compounds | | | | |
|---|---|---|---|---|---|
| No. | Compound | MW/FW | Mols | Weight (g) | Mol ratio |
| 1. | mPEG1900 (Alfa Aesar, Lot# B12L29; Stock #: 41563) | 1900 | 0.1 | 190 | 1 |
| 2. | HMDI (Fluka, Lot#: 10317/1-40800) | 168.2 | 0.3 | 50.4 | 3 |
| 3. | Triethylamine (Aldrich Batch #: 06615BA) d = 0.726 g/mL | 101.19 | 0.3 | 30.6 | 3 |

EXAMPLE 2

Condensation of mPEG-OCONH$(CH_2)_6$—NCO and D-sorbitol. D-sorbitol was dissolved in N,N-Dimethylformamide (DMF) after slight heating to 50-55° C. This solution was added drop-wise at room temperature to a stirred solution of mPEG-OCONH$(CH_2)_6$—NCO and triethylamine dissolved in chloroform. The reaction mixture was heated to reflux temperature (~60-70° C.) and allowed to react for 6-14 hours. The reaction mixture was concentrated using a ROTAVAPOR® rotary evaporator (BÜCHI Labortechnik AG) then precipitated in PE/ether. The precipitate was re-dissolved in DMF, then precipitated in PE/ether at a 1:1 ratio. The precipitate was re-dissolved in chloroform, and then precipitated using PE/ether. The final products were dried under vacuum. The yield obtained was >80%; NMR, FTIR, and DSC analysis confirmed the production of the polymer. Table 2 below details the compounds utilized to produce this polymer.

TABLE 2

| | Starting compounds | | | | |
|---|---|---|---|---|---|
| No. | Compound | MW/FW | Mols | Weight (g) | Mol ratio |
| 4. | mPEG1900-OCONH$(CH_2)_6$—NCO | ~2068 | 0.01 | 35 | 1 |
| 5. | D-Sorbitol | 182 | 0.01 | 3 | 1 |
| 6. | Triethylamine (Aldrich, batch #: 06615BA) d = 0.726 g/mL | 101.19 | 0.3 | 5.2 | 3 |

EXAMPLE 3

Ring opening polymerization (ROP) of L-lactide in bulk. Methoxy-PEG-OCN$(CH_2)_6$NH—CO—NH-D-sorbitol-(OH)$_5$ and L-lactide were heated to 135-140° C. under nitrogen gas. Stannous octoate (Sn(Oct)$_2$), a catalyst, was dissolved in ~1 mL of toluene and added to the melt. The reaction temperature was held at ~135-140° C. for 15 hours. The reaction mixture was then dissolved in chloroform and precipitated two times in PE/ether at a 1:1 ratio. The final product was dried under vacuum under nitrogen. The yield obtained was >60%; NMR, FTIR, and DSC analysis confirmed the production of the polymer. Table 3 below details the compounds utilized to produce this polymer.

TABLE 3

Starting compounds

| No. | Compound | MW/FW | Mols | Weight (g) | Mol ratio |
|---|---|---|---|---|---|
| 7. | mPEG1900-OCONH(CH$_2$)$_6$—NCO-D-sorbitol-(OH)$_5$ | ~2250 | 0.01 | 22.50 | 1 |
| 8. | L-lactide | 144 | 0.50 | 72.0 | 50 |
| 9. | Sn(Oct)$_2$ | 405 | 0.00011-0.00016 | 0.047-0.066 | 500-700 ppm |

EXAMPLE 4

Condensation of mPEG$_5$-OCONH(CH$_2$)$_6$NH-D-sorbitol-(polylactide-OH)$_5$ with hexamethylene diisocyanate (HMDI). Methoxy-PEG-OCONH(CH$_2$)$_6$NH-D-sorbitol-(polylactide-OH)$_5$ and triethylamine (catalyst) were dissolved in 300 g chloroform at room temperature. This solution was added gradually to a stirred solution of HMDI in chloroform. The reaction temperature was raised to reflux (60-65° C.) and maintained under nitrogen gas for 4 to 6 hours. The volume of the reaction mixture was reduced by evaporation using ROTAVAPOR® rotary evaporator and the final product was precipitated two times in PE/ether at a 1:1 ratio. The final products were dried overnight in a vacuum. The yield obtained was >90%; NMR, FTIR, and DSC analysis confirmed the production of the polymer. Table 4 below details the compounds utilized to produce this polymer.

TABLE 4

Starting compounds

| No. | Compound | MW/FW | Mols | Weight (g) | Mol ratio |
|---|---|---|---|---|---|
| 10. | mPEG 1900-OCONH(CH$_2$)$_6$—NCO D-sorbitol-(lactide-OH)$_5$ | ~9425 | 0.005 | 47.13 | 1 |
| 11. | HMDI (Fluka, Lot# 10317/1-40800) b.p. 255° C. | 168.2 | 0.125 | 21 | 25 |
| 12. | Triethylamine (Aldrich, Batch #: 06615BA) d = 0.726 g/mL | 101.19 | 0.5 | 7.5 | 15 |

It will be understood that various modifications may be made to the embodiments disclosed herein. Therefore the above description should not be construed as limiting, but merely as exemplifications of some typical embodiments. Those skilled in the art will envision other modifications within the scope and spirit of the claims appended hereto.

What is claimed is:

1. A biocompatible synthetic macromer composition comprising:
    a first polymer having the structure

    R"—[R$_1$—X]$_n$ (VII)

wherein R" is selected from the group consisting of polysaccharides and polyols, R$_1$ is a poly(hydroxy) acid, X is a functional group selected from the group consisting of epoxy, halogen, isocyanate, chlorophosphates, anhydrides, and combinations thereof, and n is a number from 1 to 10; and
    a second polymer comprising a functionalized polyurethane prepolymer having the structure

    (R$_4$)$_m$—((Y)$_p$-D-(Y)$_p$)$_z$—(R$_5$)$_m$ (IX)

wherein Y is a polymer backbone, D is selected from the group consisting of cyclodextrin, sorbitol, polyphenol and polyglycerol, R$_4$ and R$_5$ can be the same or different and are selected from the group consisting of NCO, CHO, and COOH, m is a number from about 1 to about 50, p is a number from about 1 to about 30, and z is a number from about 2 to about 20.

2. A biocompatible synthetic macromer composition as in claim 1, wherein the X groups present on the first polymer are the same.

3. A biocompatible synthetic macromer composition as in claim 1, wherein the X groups present on the first polymer are different.

4. A biocompatible synthetic macromer composition as in claim 1, wherein R" comprises a polyethylene glycol.

5. A biocompatible synthetic macromer composition as in claim 1, wherein R" comprises a methoxy polyethylene glycol.

6. A biocompatible synthetic macromer composition as in claim 1, wherein R$_4$ and R$_5$ are the same.

7. A biocompatible synthetic macromer composition as in claim 1, wherein R$_4$ and R$_5$ are different.

8. A biocompatible synthetic macromer composition as in claim 1, wherein Y comprises a polyalkylene oxide.

9. A biocompatible synthetic macromer composition as in claim 8, wherein Y comprises a polyethylene glycol.

10. A biocompatible synthetic macromer composition as in claim 1, further comprising an amine cross-linker.

11. A biocompatible synthetic macromer composition as in claim 10, wherein said amine cross-linker is selected from the group consisting of diamines, aromatic amines, polyamines, and polyamidoamines.

12. A biocompatible synthetic macromer composition as in claim 1, wherein the biocompatible synthetic macromer composition further includes a component selected from the group consisting of biologically active agents and medicinal agents.

13. A biocompatible synthetic macromer composition as in claim 1, further comprising an enzyme, wherein the enzyme increases the degradation rate of the biocompatible synthetic macromer composition.

14. A method for closing a wound comprising:
    applying the biocompatible synthetic macromer composition of claim 1 to said wound; and
    allowing the biocompatible synthetic macromer composition to set thereby closing said wound.

15. The method of claim 14 wherein the wound is a surgical incision.

16. A method for filling a void in animal tissue comprising:
    applying the biocompatible synthetic macromer composition of claim 1 to said void; and
    allowing the biocompatible synthetic macromer composition to set thereby filling said void.

17. A method for adhering a medical device to a surface of animal tissue comprising the steps of:
    applying the biocompatible synthetic macromer composition of claim 1 to said device, said surface or both;
    bringing the device, biocompatible synthetic macromer composition and surface into contact with each other; and
    allowing the biocompatible synthetic macromer composition to set thereby adhering the device and surface to each other.

18. The method of claim 17 wherein said medical device is an implant.

* * * * *